United States Patent [19]

Yuki et al.

[11] Patent Number: 4,665,161

[45] Date of Patent: May 12, 1987

[54] PROCESS FOR PRODUCING HIGHLY PURIFIED HCG

[75] Inventors: Yoshikazu Yuki, Kobe; Toyohiko Nishimura, Ashiya; Hajime Hiratani, Sennan, all of Japan

[73] Assignee: Japan Chemical Research Co., Ltd., Hyogo, Japan

[21] Appl. No.: 857,511

[22] Filed: Apr. 21, 1986

Related U.S. Application Data

[63] Continuation of Ser. No. 473,941, Mar. 10, 1983.

[30] Foreign Application Priority Data

Mar. 15, 1982 [JP] Japan .................. 57-41527

[51] Int. Cl.$^4$ .............................................. C07K 3/12
[52] U.S. Cl. ................................... 530/412; 530/416; 530/418; 530/422; 530/424
[58] Field of Search ................ 530/416, 418, 422, 424

[56] References Cited

U.S. PATENT DOCUMENTS 4,196,123 4/1980 Rosemberg .................. 260/112.5 R

FOREIGN PATENT DOCUMENTS 197380 4/1983 Japan .

OTHER PUBLICATIONS

Van Hell, *Chemical Abstracts*, 83 (3), 1974, abst. No. 24700t.
Lauriere, *Chemical Abstracts*, 88 (23), 1977, abst. No. 166334d.
Tsubota et al., *Chemical Abstracts*, 89 (1), 1978, abst. No. 2739j.
Lee et al., *Chemical Abstracts*, 83 (25), 1974, abst. No. 203406y.
Okumura et al., *Chemical Abstracts*, 84, 1976, abst. No. 161407n.

*Primary Examiner*—Delbert R. Phillips
*Attorney, Agent, or Firm*—Burgess, Ryan & Wayne

[57] ABSTRACT

Crude HCG is purified by extracting with a neutral or weakly basic aqueous solution containing lower aliphatic alcohol and soluble salt, adding lower aliphatic alcohol to the extracted solution to form precipitates and the precipitates containing high purity of HCG are collected. This precipitates can be further purified by dissolving in a buffer solution, contacting the solution with a weak anion exchanger and eluting the exchanger with said buffer solution containing added salt.

14 Claims, No Drawings

PROCESS FOR PRODUCING HIGHLY PURIFIED HCG

This application is a continuation, of application Ser. No. 473,941, filed Mar. 10, 1983.

This invention relates to a process for producing human chorionic gonadotropin (hereinafter called "HCG") of high purity.

It is known that HCG contained in urine from pregnant women is extracted by a purification procedure using benzoic acid or kaolin as an adsorbent to thereby obtain several hundreds international units (IU)/mg (protein) of crude HCG. Moreover, it is known that such crude HCG is repeatedly subjected to extraction and precipitation procedures and then dialyzed to thereby obtain several thousands IU/mg (protein) of HCG with relatively high specific activity.

The present inventors conducted an extensive research for developing a process for purifying HCG in higher efficiency by a simpler procedure than the conventional methods and came to accomplish the present invention.

This inventin is directed to a process for producing highly purified HCG which comprises extracting chorionic gonadotropin of low purity with a neutral or weakly basic aqueous solution containing lower alcohol and soluble salt, adding lower aliphatic alcohol to the extracted solution and then collecting the precipitates thus formed.

This invention is also directed to a process for producing highly purified HCG which comprises extracting chorionic gonadotropin of low purity with a neutral or weakly basic aqueous solution containing lower aliphatic alcohol and soluble salt, and then adding lower aliphatic alcohol to the extracted solution, collecting the precipitates thus formed, subsequently, dissolving the precipitates in a weakly acidic or weakly basic buffer solution, contacting the solution thus obtained with a weakly basic anion exchanger, and eluting the anion exchanger with a solution made up of th said buffer solution and salt.

HCG of low purity which is employed as a raw material in the practice of this invention, is preferred to have a specific activity of several hundreds to thousands IU/mg (protein). For example, the above-mentioned crude HCG or HCG with a relatively high specific activity can be employed.

Furthermore, HCG roduced in accordance with the method described by the present inventors in the patent application formerly filed in Japan, application number 56-197380, can also be employed.

According to this method, urine from pregnant women, after removing the impurities precipitated at preferably pH 8-9, is contacted with an adsorbent consisting of a weakly acidic aluminosilicate of the formula $Al_2O_3.9SiO_2.xH_2O$ to thereby adsorb the components in the urine. The adsorbate is then eluted with alkaline aqueous solution and the eluate is adjusted to weakly acidic state, and the precipitate formed removed. From this supernatant crude HCG can be collected. Or in an alternate method, the afore-mentioned adsorbate is eluted with an aqueous solution containing lower aliphatic alcohol and soluble salt. The crude HCG can be collected from the eluate. The crude HCG has a specific activity of about 2,000-3,000 IU/mg (protein).

HCG of low purity mentioned above is extracted with a neutral or weakly basic aqueous solution, preferably having a pH of 7-8.5, which contains a lower aliphatic alcohol and salt soluble in the solution.

As the lower aliphatic alcohol, an alcohol such as methanol may be used, but ethanol is particularly preferred.

The concentration of alcohol in the aqueous solution is preferably 55-57% for ethanol and 60-80% for methanol.

The preferred soluble salt for the lower aliphatic alcohol is, for example, ammonium acetate, and its preferred concentration in the aqueous solution is approximately 10%.

The pH of the solution for extraction is adjusted to either neutral or weakly basic, preferably pH 7-8.5.

In general, the quantity of the extracted solution employed is preferably 10 to 20-fold to that of HCG material, and the extraction is carried out preferably at a temperature as low as possible.

The extracted solution is then centrifuged and admixed with additional lower aliphatic alcohol to thereby precipitate HCG for collection.

In this way, HCG which is much higher in purity than that of the raw material can be obtained with a high yield of more than 90%. For example, if HCG of 2,000-2,500 IU/mg (protein) is employed as a raw material, HCG product of 6,000-7,000 IU/mg (protein) can be obtained. This specific activity is the same or even superior than that of purified HCG heretofore known.

It was then found that HCG obtained by the above methods can be further purified by employing a weakly basic anion exchanger.

For this purpose, precipitates of HCG collected in the afore-mentioned procedure is dissolved in a weakly acidic or weakly basic buffer solution, preferably at pH 5.5-9 or more preferably at pH 6-7.5. The solution is then contacted with a weakly basic ion exchanger.

As the buffer solution, a phosphate buffer solution and the like may be employed.

As the weakly basic anion exchanger, for example, DEAE (diethylaminoethyl) Cellulose, DEAE Sephadex, and DEAE Sepharose produced by Phamacia Fine Chemicals AB (Uppsala, Sweden) may be employed.

By contact with the ion exchanger, HCG in the solution is adsorbed, and it can be eluted therefrom. Elution is carried out using the above buffer solution with salt added.

As the salt, for example, sodium chloride may be employed, and its concentration in the buffer solution is preferred to be approximately 0.05-0.3M.

Subject to the above procedure, the purity of HCG is significantly raised with a high yield of about 80-85%. For instance, the purity of HCG of 6,000-7,000 IU/mg (protein) can be raised to 13,000-16,000 IU/mg (protein).

The following examples are further illustrative of this invention.

EXAMPLE 1

50 liters of urine from pregnant women of 2nd to 6th month pregnancy were adjusted to pH 8.5 with 4N-sodium hydroxide solution, and the resultant precipitates were filtered off. The filtrate was adjusted to pH 3.5 with 6N-hydrochloric acid and introduced into a column 10 cm in diameter at a rate of 2 liter/hour. The column contained 100 grams of synthetic aluminosilicate (KYOWAAD ® 700 (50-100 mesh) produced by Kyowa Chemical industries, Ltd. (Tokyo, Japan)). The adsorbent was then washed with 1.0 liter of water, and elution was carried out with 1.0 liter of 40% ethanol containing 10% ammonium acetate. To 500 ml of the eluate, 3-fold its volume or 95% ethanol was added, whereby HCG was precipitated.

The yield of HCG was 296,000 IU, the specific activity thereof was 3,000 IU/mg (protein) and the percent yield was 85%.

500,000 IU of this crude HCG was extracted with 110 ml of 60% ethanol containing 9% ammonium acetate (pH 8.0) during 24 hours at 4° C. Subsequently, centrifugation was carried out, and 200 ml of ethanol was added to 100 ml of the supernatant, thereby precipitating HCG and centrifuging the precipitates for collection.

The specific activity of HCG thus obtained was 7,000 IU/mg (protein) and the yield thereof was 90%.

EXAMPLE 2

As in the procedure described in Example 1, 50 liters of pregnant urine from pregnant women of 2nd to 6th month pregnancy was treated at pH 8.5 and was further adjusted to pH 3.5 with diluted hydrochloric acid. The solution was then contacted with 500 grams of the same synthetic aluminosilicate (50–100 meshes) as used in Example 1 for 2 hours. The mixture was allowed to stand and the supernatant was separated from the adsorbent. The adsorbent was washed with 5.0 liters of water into a column of 10 cm in diameter and was further washed with 5.0 liters of water. Elution was carried out with 5.0 liters of 2N-aqueous sodium carbonate and 8.0 liters of the eluate was adjusted to pH 5.0 with diluted hydrochloric acid. After the resultant precipitates were centrifuged, ammonium sulfate was added to 50% saturation, whereby HCG was precipitated.

The yield was 90.2% and the specific activity was 2,000 IU/mg (protein).

2,000,000 IU of this crude HCG was extracted with 150 ml of 70% methanol containing 10% ammonium acetate (pH 8.0) for 24 hours at 4° C. Subsequently, centrifugation was carried out. 270 ml of methanol was added to 135 ml of supernatant, thereby precipitating HCG. The precipitates were collected by centrifugation.

The specific activity of HCG thus obtained was 6,000 IU/mg (protein) and the yield thereof was 93%.

EXAMPLE 3

HCG obtained in Example 1 was dissolved in 0.01m phosphate buffer solution (pH 7.0) and was intraduced into a DEAE Cellulose column (1.2×15 cm) which had previously been buffered with the above-mentioned buffer solution. After non-adsorption section was marked off, elution of HCG was carried out in accordance with the step-wise method using a buffer solution prepared by adding 0.1M sodium chloride to the above-mentioned buffer solution.

The specific activity of the HCG thus obtained was 16,000 IU/mg (protein) and the yield thereof was 85%.

EXAMPLE 4

HCG obtained in Example 2 was dissolved in 0.005M phosphate buffer solution (pH 7.5) and was introduced into a DEAE Sephadex column (2×15 cm) of 3 g which was previously buffered with the mentioned phosphate buffer solution. After non-adsorption section was marked off, elution was carried out in accordance with Step-wise method using a buffer solution prepared by adding 0.15M sodium chloride to the above-mentioned buffer solution.

The specific activity of HCG thus obtained was 14,000 IU/mg (protein) and the yield thereof was 80%.

For determination of HCG, Chorionic Gonadotropin Reference Standard of Japanese Pharmacopeia was employed and the test was carried out as directed under the rat ovarian weight method of Japanese Pharmacopeia.

The quantity of protein was determined by the method of Lowry-Folin employing BSA as the standard.

We claim:

1. A process for producing highly purified HCG which comprises the steps of:
   (1) contacting urine from pregnant women with an adsorbent of weakly acidic aluminosilicates having the formula of $Al_2O_3.9H_2O.xH_2$; and either:
      (a) eluting the adsorbent with an aqueous solution containing a lower aliphatic alcohol and a soluble salt, and collecting low purity chorionic gonadotropine from the eluate; or
      (b) eluting the adsorbent with an alkaline aqueous solution, adjusting the eluate to a weakly acidic state, removing the precipitate thus formed, and collecting low purity chorionic gonadotropine from the supernatent; and,
   (2) extracting the low purity chorionic gonadotropine obtained from step (a) or (b) with a neutral or weakly acidic aqueous solution containing ethanol in a concentration of from about 55 to about 60%, or methanol in a concentration of from about 60 to about 80% and a soluble salt; adding a lower aliphatic alcohol to the extracted solution; and thereafter collecting the precipitate thus formed.

2. A process according to claim 1 wherein both soluble salts are ammonium acetate.

3. A process according to claim 1 wherein the low purity of chorionic gonadotropine is extracted with an aqueous solution having a pH of 7 to 8.5 and containing ethanol or methanol and approximately 10% of ammonium acetate, and thereafter adding ethanol or methanol to the extract and thereafter collecting the precipitate thus formed.

4. A process for producing highly purified HCG which comprises the steps of:
   (1) contacting urine from pregnant women with an adsorbent of weakly acidic aluminosilicates having the formula of $Al_2O_3.9H_2O.xH_2O$; and either:
      (a) eluting the adsorbent with an aqueous solution containing a lower aliphatic alcohol and a soluble salt, collecting low purity chorionic gonadotropine from the eluate; or
      (b) eluting the adsorbent with alkaline aqueous solution, adjusting the eluate to a weakly acidic state, removing the precipitate thus formed, collecting low purity chorionic gonadotropine from the supernatant;
   (2) extracting the low purity chorionic gonadotropine with a neutral or weakly acidic aqueous solution containing ethanol in a concentration of 55 to 60%, or methanol in a concentration of 60 to 80% and a soluble salt; adding lower aliphatic alcohol to the extracted solution; and then collecting the precipitate thus formed;
   (3) dissolving the precipitate in a weakly acidic or weakly basic buffer solution; contacting the solution with a weakly basic anion exchanger; and then eluting the exchanger with a solution made up of the said buffer solution and a salt.

5. The process according to claim 4 wherein the buffer solution has a pH of from 5.5 to 9.

6. The process according to claim 4 wherein the buffer solution is a phosphate buffer solution.

7. The process according to claim 4 wherein in step (3) said salt is sodium chloride and its concentration in said buffer solution is from 0.05 to 0.3M.

8. A process according to claim 4 wherein the anion exchanger has diethylamino groups.

9. A process according to claim 4 wherein the anion exchanger has diethylaminoethyl groups.

10. The process according to claim 4 wherein in step (1)(a) the lower aliphatic alcohol is methanol.

11. The process according to claim 4 wherein in step (1)(a) the lower aliphatic alcohol is ethanol.

12. The process according to claim 4 wherein in step (1)(a) the soluble salt is ammonium acetate.

13. A process for producing HCG having a specific activity of 13,000 to 16,000 IU/mg (protein) which comprises the steps of:
 (1) contacting urine from pregnant women with an adsorbent of weakly acidic aluminosilicates having the formula of $Al_2O_3.9H_2O.xH_2O$; eluting the adsorbent with an aqueous solution containing a lower aliphatic alcohol and a soluble salt, and collecting low purity chorionic gonadotropine from the eluate;
 (2) extracting the low purity chorionic gonadotropine with a neutral or weakly basic aqueous solution containing ethanol in a concentration of 55 to 60%, or methanol in a concentration of 60 to 80% and a soluble salt; adding a lower aliphatic alcohol to the extracted solution to cause formation of a precipitate; and then collecting the precipitate thus formed; and
 (3) dissolving the precipitate in a weakly acidic or weakly basic buffer solution; contacting the solution with a weakly basic anion exchanger; and then eluting the exchanger with a solution made up of the said buffer solution and a salt and recovering said HCG.

14. A process for producing HCG having a specific activity of 13,000 to 16,000 IU/mg (protein) which comprises the steps of:
 (1) contacting urine from pregnant women with an adsorbent of weakly acidic aluminosilicates having the formula of $Al_2O_3.9H_2O.xH_2O$; eluting the adsorbent with alkaline aqueous solution, adjusting the eluate to a weakly acidic state, removing the precipitate thus formed, and collecting low purity chorionic gonadotropine from the supernatant;
 (2) extracting the low purity chorionic gonadotropine with a neutral or weakly basic aqueous solution containing ethanol in a concentration of 55 to 60%, or methanol in a concentration of 60 to 80% and a soluble salt; adding a lower aliphatic alcohol to the extracted solution to cause formation of a precipitate; and then collecting the precipitate thus formed; and
 (3) dissolving the precipitate in a weakly acidic or weakly basic buffer solution; contacting the solution with a weakly basic anion exchanger; and then eluting the exchanger with a solution made up of the said buffer solution and a salt and recovering said HCG.

* * * * *